United States Patent [19]

Hoy Jr.

[11] Patent Number: Plant 5,360

[45] Date of Patent: Dec. 4, 1984

[54] ROSE NAMED LADY DIANA

[75] Inventor: Lowell L. Hoy Jr., Richmond, Ind.

[73] Assignee: Joseph H. Hill Company, Richmond, Ind.

[21] Appl. No.: 505,833

[22] Filed: Jun. 20, 1983

[51] Int. Cl. ..... A01H 5/00

[52] U.S. Cl. ..... Plt./18

[58] Field of Search ..... Plt./18, 14

*Primary Examiner*—Robert E. Bagwill

*Attorney, Agent, or Firm*—Charles W. Rummler

[57] ABSTRACT

A rose cultivar intended for greenhouse culture for cut flower production, the new plant being distinguished by its abundant and continuous production of medium large flowers of a soft clear shade of pastel pink borne on long, medium strong stems and having an excellent vase life. As a greenhouse rose, this plant has a free and vigorous growth habit, upright and much branched, with abundant foliage having a high winter production of flowers for the cut flower market.

1 Drawing Figure

BACKGROUND OF THE NEW PLANT

This new variety of rose plant originated at Richmond, Ind., as a seedling resulting from my crossing of the rose variety "Sonia" (U.S. Plant Pat. No. 3,095) with the rose variety "Caresse" (U.S. Plant Pat. No. 3,126) as the pollen parent. This crossing was done in the Spring of 1976 and the first flower was bloomed in the Fall of 1977. The object of this crossing was to produce a hybrid tea rose, in the color range in which the two parents fall, that would provide long stems and possess good productivity the year round for cut flowers. Because of the distinctiveness of the flower of this plant and its advantageous growth habit, I reproduced this plant at Richmond, Ind., to test its retention of its distiguishing charcteristics and propagation of this new plant through successive generations, by grafting at Richmond, Ind., and by budding at Pleasanton, Calif., has demonstrated that the distinctive characteristics of the new variety hold true from generation to generation and appear to be firmly fixed.

DESCRIPTION OF THE DRAWING

My new variety of rose plant is illustrated by the accompanying drawing which shows, in full color, face views of a newly opened flower and a mature blossom, specimens of buds in various stages of opening, typical specimens of leaves, specimens of inside petals of the fully opened flower, and outside petals of the same, a specimen of young wood and leaves, and a specimen of mature wood. The colors shown are believed to be as true as is reasonably possible to obtain through conventional photographic procedures.

DESCRIPTION OF THE NEW PLANT

The following is a detailed description of my new variety of rose plant based upon observations of greenhouse plants grown in greenhouse at Richmond, Ind., the color designations being made according to The Horticultural Colour Chart (HCC) produced by Robert S. Wilson in collaboration with The British Colour Counsel and published by The Royal Horticultural Society of London, England, and in some particulars, according to Koster's Color Guide (K).

THE PLANT

Origin: Seedling identified as No. 77-2P.

Parentage:

*Seed parent.*—Sonia, U.S. Plant Pat. No. 3,095.

*Pollen parent.*—Caresse, U.S. Plant Pat. No. 3,126.

Classification: Hybride tea type for greenhouse culture for cut flower production.

Form: Bush.

Growth: Free and vigorous.

Habit: Upright and much branched.

Canes: Medium in diameter.

Main stems:

*Color.*—Spinach Green 0960 (W).

*Thorns.*—Several of medium length, downwardly hooked and with a short, narrow base. Color: Violet Lilac, Plate No. 47 (K).

*Prickles.*—Very few. Color: Violet Lilac, Plate No. 47 (K).

*Hairs.*—None.

Branches:

*Color.*—Spinach Green 0960 (W).

*Thorns.*—Several of medium length, downwardly hooked and with a short, narrow base. Color: Bistre, Plate No. 93 (K).

*Prickles.*—Very few. Color: Bistre, Plate No. 93 (K).

*Hairs.*—None.

New shoots:

*Color.*—Scheeles Green 860/3 with Delft Rose 020/2 shading the leaves (W).

*Thorns.*—Very few of medium length and downwardly hooked with a very short, narrow base. Color: Fire Red 15/2 (W).

*Prickles.*—Few. Color: Fire Red 15/3 (W).

*Hairs.*—None.

Foliage:

*Quantity.*—Moderately abundant.

*Leaves.*—Compound and odd pinnate. Size: Medium.

*Leaflets.*—3 To 7. Shape: Ovoid with acuminate apex, obtuse base and simply serrate margin. Texture: Moderately heavy. Color: Young Leaves: Upper surface — Spinach Green 0960/2 shaded with Garnet Lake 828/1 (W). Under surface — Fern Green 0862/2 shaded with Garnet Lake 828/1 (W). Mature Leaflets: Upper surface — Spinach Green 0960 (W). Under surface — Spinach Green 0960/2 (W).

*Rachis.*—Heavy. Upper Side: Hairy. Under Side: Prickly.

*Stipules.*—Wide and long with points which are of medium length and turning out at an angle of less than 45° with the stem.

THE BUD

Before calyx breaks:

*Size.*—Medium large.

*Form.*—Long pointed with a conspicuous neck and foliaceous appendages on the surface of the bud having much cut parts extending beyond the tip of the bud a distance equal to about one-quarter or more of the bud length.

*color.*—Spinach Green 0960/2 (W).

As the calyx breaks:

*Outside petal color.*—Begonia 619/3 tinted with Begonia 619/2 (W).

As the first petal opens:

*Bud size.*—Medium large.

*Bud form.*—Long pointed.

*Color of petal.*—Outside — Nearest color is Pure White, Plate No. 1 (K), tinted with Begonia 619/3 (W). Inside — Nearest color is Pure White, Plate No. 1 (K), tinted with Begonia 619/2 (W).

Character of Opening: The bud opens well in greenhouse and no unusual characteristics have been noted with respect to the effect of weather.

Sepals: Permanent and of medium length.

*Shape.*—Spear shaped and recurved.

*Color.*—Inside — Pod Green 061/1 (W) tinted with Fern Green 0862/1 (W) overlaid with White fuzz. Outside — Spinach Green 0960/2 (W).

Peduncle:

*Size.*—Long in length and of medium diameter with strong and erect character.

*Bark.*—Entirely smooth. Color: Spinach Green 0960 (W).

*Thorns, prickles and hairs.*—The peduncle has none of these.

THE FLOWER

Blooming habit: Free, abundant and continuous, in greenhouse.

Size: Medium large when fully opened with a diameter of about 4 to 5 inches.

Form: Full and high centered at first with petals tightly rolled outward and becoming open and high centererd with petals loosely rolled outward at maturity.

Borne: One to three to a stem in regular clusters on long, medium strong stems. (May be disbudded for commercial use.)

Petalage: Double, with from 35 to about 40 petals arranged regularly.

*Shape.*—Outside petals — Obovate with retuse apex, some having a single notch. Intermediate petals — Obovate with retuse apex and some having a single notch. Inside petals — Obovate with mucronate apex, some of which have a single notch.

*Texture.*—Soft and moderately thick.

*Aspect.*—Velvety on both inside and outside surfaces.

Color: The following is the color description of a newly opened greenhouse rose in the month of December 1982 at Richmond, Ind.

*Outside petals.*—Outer surface — Nearest color is Pure White, Plate No. 1 (K), tinted with Begonia, 619/3 (W). Inside surface — Nearest color is Pure White, Plate No. 1 (K), tinted with Begonia, 619/1, some petals being striped with Scheeles Green 860/3 (W).

*Intermediate petals.*—Outside surface — Nearest color is Pure White, Plate No. 1 (K), tinted with Begonia, 619/3 (W). Inside surface — Nearest color is Pure White, Plate No. 1 (K), tinted with Begonia, 619/1 (W).

*Inner petals.*—Both the outer and inner surfaces have the same color characteristics as the intermediate petals.

This description was made from a rose that was open for three days in greenhouse in the month of December 1982 at Richmond, Ind.

*Outside petals.*—Outer surface — Nearest color is Pure White, Plate No. 1 (K), tinted with Begonia, 619/3 (W). Inside surface — The same as the outer surface.

*Intermediate and inner petals.*—The intermediate petals and the inner petals have the same color characteristics as the outside petals.

*General color effect.*—Newly opened flower — Pure White, Plate No. 1 (K), tinted with Begonia 619/2 (W). Three days opened flower — Pure White, Plate No. 1 (K), tinted with Begonia 619/3 (W).

*Fragrance.*—Slight tea.

*Persistence.*—The petals hang on and dry and no unusual characteristics have been noted with respect to the effect of weather.

*Lasting quality.*—Six to seven days in April at living room temperatures.

REPRODUCTIVE ORGANS

Stamens: Many in number arranged regularly about the pistils and mixed with petaloids tucked in the calyx.

*Filaments.*—Of medium length and many with anthers. Color: Begonia 619/1 (W).

*Anthers.*—Of medium size and all open at once. Color: Indian Yellow 6/2 (W).

*Pollen.*—Sparse in quantity. Color: Buttercup Yellow 5/2 (W).

Pistils: Few in number.

*Styles.*—Of medium and uneven length, moderately thin and bunched. Color: Primrose Yellow 601/3 washed with Geranium Lake 20/2 toward the stigma (W).

*Stigmas.*—Color — Barium Yellow 503/3 (W).

Ovaries: All encased in calyx.

Seeds: None noted.

This new rose variety is an improvement over its seed parent in that the flower is larger with much longer stems, the new flower being borne on medium-to-long, sturdy, straight upright stems. Also, the foliage of the new plant is profuse which enhances the color and elegant shape of the bud and opening flower. This new cultivar is also considered to be a better variety than its pollen parent in that it has a much more attractive bud and clearer appearing outer guard petals. Also, the new variety has substantially higher winter production than its pollen parent which is a decided advantage from the commercial standpoint.

This new cultivar is similar to "Royal Highness" (U.S. Plant Pat. No. 2,032). "Royal Highness", however, is a garden hybrid tea whereas this new cultivar is more adapted to greenhouse cut flower production. "Kyria" (U.S. Plant Pat. No. 4,017), which is a sport of the seed parent of this new cultivar, is also similar in color but it is an intermediate sized greenhouse rose whereas this new cultivar is a hybrid tea.

I claim:

1. A new and distinct rose plant cultivar, substantially as herein shown and described, characterized by its abundant, profuse and continuous production of medium large flowers having a soft, clear shade of pastel pink color borne on medium-to-long straight upright stems with profuse foliage.

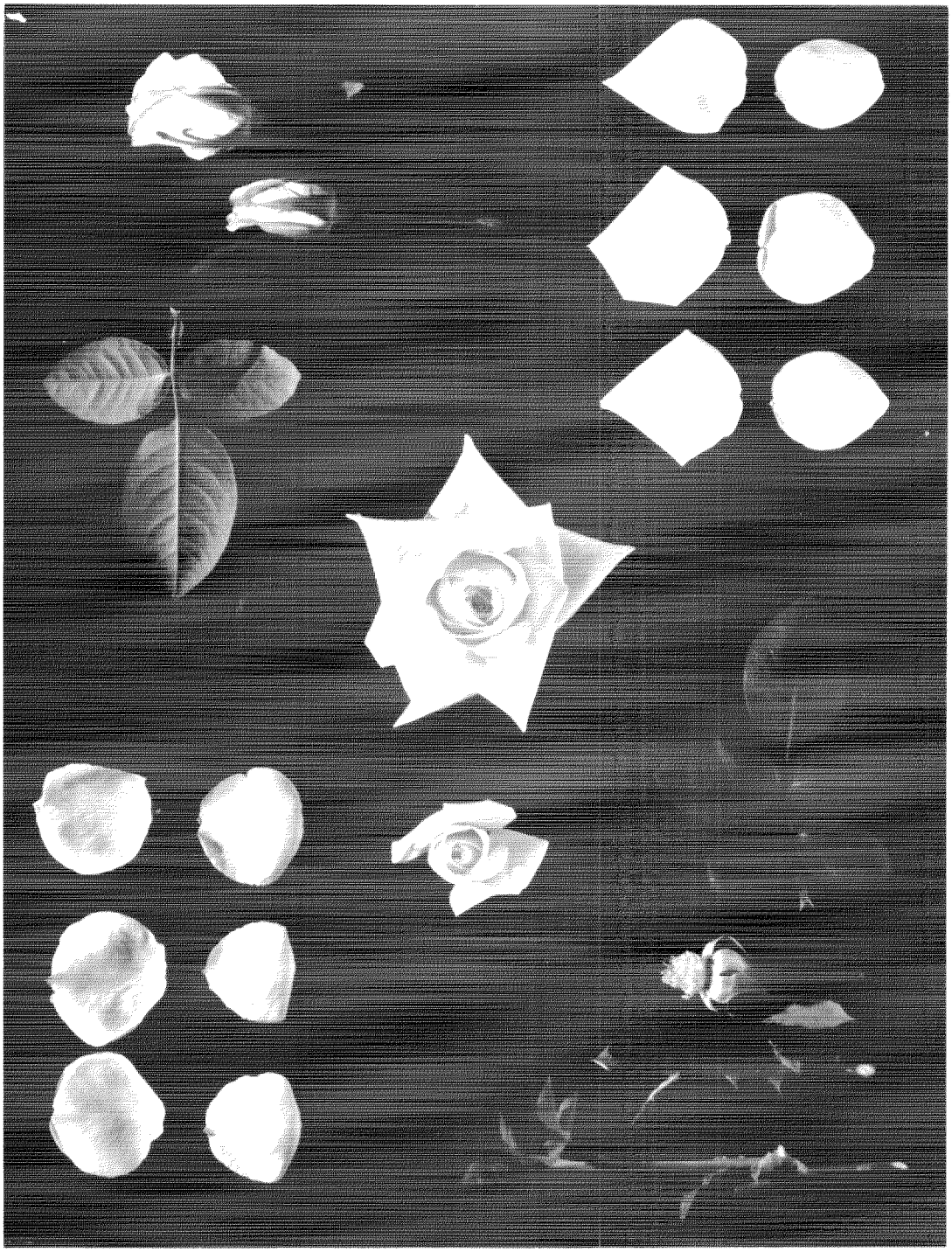

* * * * *